US010478191B2

(12) United States Patent
Penna

(10) Patent No.: US 10,478,191 B2
(45) Date of Patent: Nov. 19, 2019

(54) BUTTRESS ATTACHMENT FOR CIRCULAR STAPLING DEVICE

(71) Applicant: Covidien LP, Mansfield, MA (US)

(72) Inventor: Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 586 days.

(21) Appl. No.: 15/225,944

(22) Filed: Aug. 2, 2016

(65) Prior Publication Data

US 2016/0338704 A1 Nov. 24, 2016

Related U.S. Application Data

(62) Division of application No. 13/758,120, filed on Feb. 4, 2013, now Pat. No. 9,414,839.

(51) Int. Cl.
*A61B 17/072* (2006.01)
*A61B 17/115* (2006.01)
(Continued)

(52) U.S. Cl.
CPC ...... *A61B 17/1155* (2013.01); *A61B 17/0682* (2013.01); *A61B 17/072* (2013.01);
(Continued)

(58) Field of Classification Search
CPC ............. A61B 17/068; A61B 17/072; A61B 17/07207; A61B 17/07292; A61B 17/115;
(Continued)

(56) References Cited

U.S. PATENT DOCUMENTS 3,054,406 A   9/1962  Usher
3,079,606 A   3/1963  Bobrov et al.
(Continued)

FOREIGN PATENT DOCUMENTS

CA   2282761 A1   9/1998
CA   2667434 A1   5/2008
(Continued)

OTHER PUBLICATIONS

European Office Action corresponding to counterpart European Appln. No. Ep 15 17 4146.9 dated May 15, 2017.
(Continued)

*Primary Examiner* — Scott A Smith

(57) ABSTRACT

A circular stapling device includes a circular anvil assembly and a circular cartridge assembly. The anvil assembly includes a cap and head. The cap is movable relative to the head. The head supports a crush ring member that is movable into engagement with the cap to move the cap to an unapproximated position relative to the head to release a portion of an anvil buttress member supported between the anvil cap and the anvil head. The cartridge assembly includes a housing, a pusher member, a retaining ring member, and a fastener cartridge. The retaining ring member releasably secures a portion of a cartridge buttress member to one or both of the housing and the fastener cartridge. The retaining ring member releases the cartridge buttress member when the retaining ring member moves from a radially constricted condition to a radially expanded condition in response to a movement of the pusher member.

8 Claims, 10 Drawing Sheets

(51) Int. Cl.
*A61B 17/068* (2006.01)
*A61B 17/00* (2006.01)

(52) U.S. Cl.
CPC .. *A61B 17/07207* (2013.01); *A61B 17/07292* (2013.01); *A61B 17/068* (2013.01); *A61B 17/115* (2013.01); *A61B 2017/00477* (2013.01); *A61B 2017/00862* (2013.01); *A61B 2017/07214* (2013.01); *A61B 2017/07257* (2013.01); *A61B 2017/07271* (2013.01); *Y10T 29/49815* (2015.01)

(58) Field of Classification Search
CPC ...... A61B 17/1155; A61B 2017/07214; A61B 2017/07271; A61B 2017/07257
USPC .............. 227/19, 175.1, 176.1, 175.2, 180.1; 606/139, 151, 153, 219
See application file for complete search history.

(56) References Cited

U.S. PATENT DOCUMENTS

| | | |
|---|---|---|
| 3,124,136 A | 3/1964 | Usher |
| 3,490,675 A | 1/1970 | Green et al. |
| 3,499,591 A | 3/1970 | Green |
| 3,797,494 A | 3/1974 | Zaffaroni |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,142,933 A | 11/2000 | Longo et al. |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,610,006 B1 | 8/2003 | Amid et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |

(56) References Cited

U.S. PATENT DOCUMENTS

| | | |
|---|---|---|
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,983 B2 | 10/2011 | Chu et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,328,111 B2 | 5/2016 | Zhou et al. |
| 9,351,729 B2 | 5/2016 | Orban, III et al. |
| 9,358,005 B2 | 6/2016 | Shelton, IV et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |

(56) References Cited

U.S. PATENT DOCUMENTS

| | | |
|---|---|---|
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0028243 A1 | 3/2002 | Masters |
| 2002/0091397 A1 | 7/2002 | Chen |
| 2002/0165559 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0220592 A1* | 11/2004 | Mueller ............ A61B 17/0057 606/151 |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0251164 A1* | 11/2005 | Gifford, III .......... A61B 17/064 606/153 |
| 2005/0283256 A1 | 12/2005 | Sommerich et al. |
| 2006/0004407 A1 | 1/2006 | Hiles et al. |
| 2006/0025816 A1 | 2/2006 | Shelton |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0243707 A1 | 9/2010 | Olson et al. |
| 2010/0243708 A1 | 9/2010 | Aranyi |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0174099 A1 | 7/2011 | Ross et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2011/0282446 A1* | 11/2011 | Schulte ............ A61B 17/00491 623/11.11 |
| 2012/0012638 A1* | 1/2012 | Huang ............ A61B 17/07207 227/176.1 |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241499 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |

(56) References Cited

U.S. PATENT DOCUMENTS

| | | |
|---|---|---|
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Colson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0224686 A1 | 8/2014 | Aronhalt et al. |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2016/0045200 A1 | 2/2016 | Willman |
| 2016/0128694 A1 | 5/2016 | Baxter, III et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| CN | 101310680 A | 11/2008 |
| CN | 101332110 A | 12/2008 |
| DE | 1602563 U | 3/1950 |
| DE | 19924311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1828820 A1 | 9/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2008595 A2 | 12/2008 |
| EP | 2039308 A2 | 3/2009 |
| EP | 2090231 A1 | 8/2009 |
| EP | 2090244 A2 | 8/2009 |
| EP | 2090252 A2 | 8/2009 |
| EP | 2163211 A2 | 3/2010 |
| EP | 2189121 A1 | 5/2010 |
| EP | 2198787 A1 | 6/2010 |
| EP | 2236098 A2 | 10/2010 |
| EP | 2236099 A1 | 10/2010 |
| EP | 2258282 A2 | 12/2010 |
| EP | 2292276 A2 | 3/2011 |
| EP | 2311386 A2 | 4/2011 |
| EP | 2436348 A1 | 4/2012 |
| EP | 2462880 A2 | 6/2012 |
| EP | 2491867 A1 | 8/2012 |
| EP | 2497431 A1 | 9/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |
| EP | 2644125 A2 | 10/2013 |
| EP | 2762091 A2 | 8/2014 |
| EP | 2769687 A1 | 8/2014 |
| JP | 2000166933 A | 6/2000 |
| JP | 2002202213 A | 7/2002 |
| JP | 2007124166 A | 5/2007 |
| WO | 9005489 A1 | 5/1990 |
| WO | 9516221 A1 | 6/1995 |

(56) References Cited

FOREIGN PATENT DOCUMENTS

| | | |
|---|---|---|
| WO | 9622055 A1 | 7/1996 |
| WO | 9701989 A1 | 1/1997 |
| WO | 9713463 A1 | 4/1997 |
| WO | 9817180 A1 | 4/1998 |
| WO | 9945849 A1 | 9/1999 |
| WO | 03082126 A1 | 10/2003 |
| WO | 03088845 A2 | 10/2003 |
| WO | 03094743 A1 | 11/2003 |
| WO | 03105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 79585 dated Dec. 11, 2017.
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l, Appln No. EP 12 198 776.2 dated Apr. 7, 2015.
European Office Action corresponding to counterpart Int'l, Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 48145 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Extended European Search Report issued in corresponding European Appln. No. 14153610.2 dated Jul. 17, 2017.
Australian Examination Report issued in corresponding Australian Appln. No. 2014200074 dated Jul. 20, 2017.
European Search Report corresponding to EP 05 02 2585.3, completed Jan. 25, 2006 and dated Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and dated Jan. 11, 2007; 10 pages.
International Search Report corresponding to International Application No. PCT/US2005/ 36740, completed Feb. 20, 2007 and dated Mar. 23, 2007; 8 pages.
International Search Report corresponding to International Application No. PCT/US2007/022713, completed Apr. 21, 2008 and dated May 15, 2008; 1 page.
International Search Report corresponding to International Application No. PCT/US2008/002981, completed Jun. 9, 2008 and dated Jun. 26, 2008; 2 pages.
European Search Report corresponding to EP 08 25 1779, completed Jul. 14, 2008 and dated Jul. 23, 2008; 5 pages.
European Search Report corresponding to EP 08 25 1989.3, completed Mar. 11, 2010 and dated Mar. 24, 2010; 6 pages.
European Search Report corresponding to EP 10 25 0639.1, completed Jun. 17, 2010 and dated Jun. 28, 2010; 7 pages.
European Search Report corresponding to EP 10 25 0715.9, completed Jun. 30, 2010 and dated Jul. 20, 2010; 3 pages.

(56) References Cited

OTHER PUBLICATIONS

European Search Report corresponding to EP 05 80 4382.9, completed Oct. 5, 2010 and dated Oct. 12, 2010; 3 pages.
European Search Report corresponding to EP 10 25 1437.9, completed Nov. 22, 2010 and dated Dec. 16, 2010; 3 pages.
European Search Report corresponding to EP 09 25 2897.5, completed Feb. 7, 2011 and dated Feb. 15, 2011; 3 pages.
European Search Report corresponding to EP 10 25 0642.5, completed Mar. 25, 2011 and dated Apr. 4, 2011; 4 pages.
European Search Report corresponding to EP 11 18 8309.6, completed Dec. 15, 2011 and dated Jan. 12, 2012; 3 pages.
European Search Report corresponding to EP 12 15 2229.6, completed Feb. 23, 2012 and dated Mar. 1, 2012; 4 pages.
European Search Report corresponding to EP 12 15 0511.9, completed Apr. 16, 2012 and dated Apr. 24, 2012; 7 pages.
European Search Report corresponding to EP 12 15 2541.4, completed Apr. 23, 2012 and dated May 3, 2012; 10 pages.
European Search Report corresponding to EP 12 16 5609.4, completed Jul. 5, 2012 and dated Jul. 13, 2012; 8 pages.
European Search Report corresponding to EP 12 15 8861.0, completed Jul. 17, 2012 and dated Jul. 24, 2012; 9 pages.
European Search Report corresponding to EP 12 16 5878.5, completed Jul. 24, 2012 and dated Aug. 6, 2012; 8 pages.
Extended European Search Report corresponding to EP 12 19 1035.0, completed Jan. 11, 2013 and dated Jan. 18, 2013; 7 pages.
Extended European Search Report corresponding to EP 12 18 6175.1, completed Jan. 15, 2013 and dated Jan. 23, 2013; 7 pages.
Extended European Search Report corresponding to EP 12 19 1114.3, completed Jan. 23, 2013 and dated Jan. 31, 2013; 10 pages.
Extended European Search Report corresponding to EP 12 19 2224.9, completed Mar. 14, 2013 and dated Mar. 26, 2013; 8 pages.
Extended European Search Report corresponding to EP 12 19 6911.7, completed Apr. 18, 2013 and dated Apr. 24, 2013; 8 pages.
Extended European Search Report corresponding to EP 08 72 6500.5, completed Feb. 20, 2014 and dated Mar. 3, 2014; (7 pp).
Extended European Search Report corresponding to EP 13 19 5919.9, completed Feb. 10, 2014 and dated Mar. 3, 2014; (7 pp).
Extended European Search Report corresponding to EP 13 19 2123.1, completed Jan. 30, 2014 and dated Feb. 10, 2014; (8 pp).
Extended European Search Report corresponding to EP 13 19 6816.6, completed Mar. 28, 2014 and dated Apr. 9, 2014; (9 pp).
Extended European Search Report corresponding to EP 13 19 4995.0, completed Jun. 5, 2014 and dated Jun. 16, 2014; (5 pp).
Extended European Search Report corresponding to EP 13 19 5019.8, completed Mar. 14, 2014 and dated Mar. 24, 2014; (7 pp).
Extended European Search Report corresponding to EP 13 19 2111.6, completed Feb. 13, 2014 and dated Feb. 27, 2014; (10 pp).
Extended European Search Report corresponding to EP 13 19 7958.5, completed Apr. 4, 2014 and dated Apr. 15, 2014; (8 pp).
Extended European Search Report corresponding to EP 14 15 6342.9, completed Jul. 22, 2014 and dated Jul. 29, 2014; (8 pp).
Extended European Search Report corresponding to EP 14 15 7195.0, completed Jun. 5, 2014 and dated Jun. 18, 2014; (9 pp).
Extended European Search Report corresponding to EP 12 19 6904.2, completed Mar. 28, 2013 and dated Jul. 26, 2013; 8 pages.
Extended European Search Report corresponding to EP 12 19 8749.9, completed May 21, 2013 and dated May 31, 2013; 8 pages.
Extended European Search Report corresponding to EP 07 00 5842.5, completed May 13, 2013 and dated May 29, 2013; 7 pages.
Extended European Search Report corresponding to EP 12 19 8776.2, completed May 16, 2013 and dated May 27, 2013; 8 pages.
Extended European Search Report corresponding to EP 13 15 6297.7, completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Chinese First Office Action corresponding to counterpart Int'l Appln. No. CN 2013107068710 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 2014100284624 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016 X.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.

(56) References Cited

OTHER PUBLICATIONS

European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.

* cited by examiner

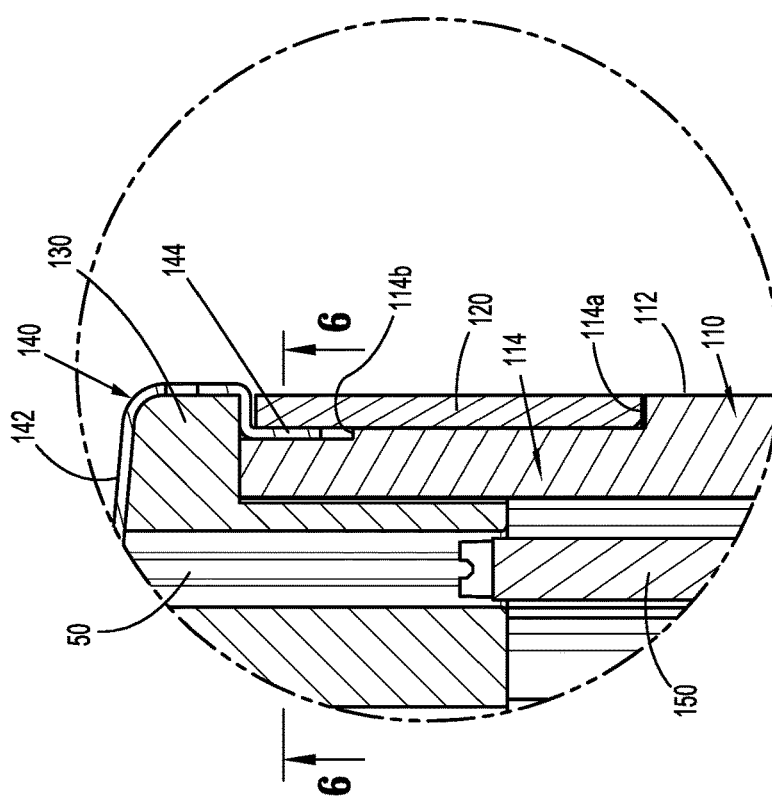
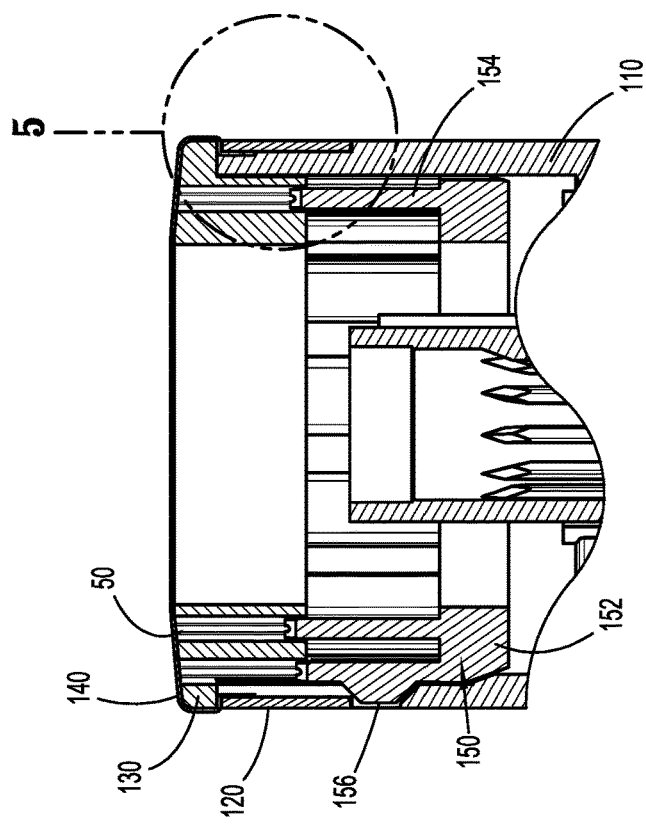
FIG. 5
FIG. 4

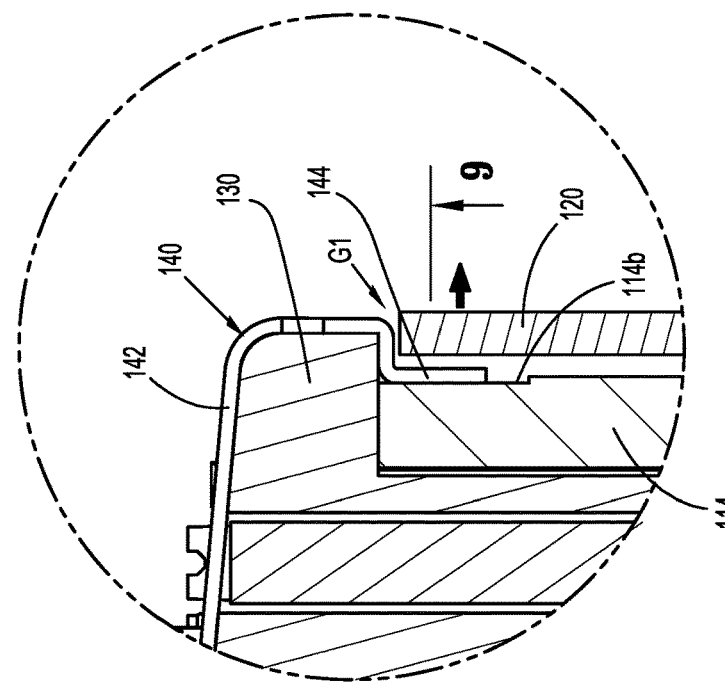
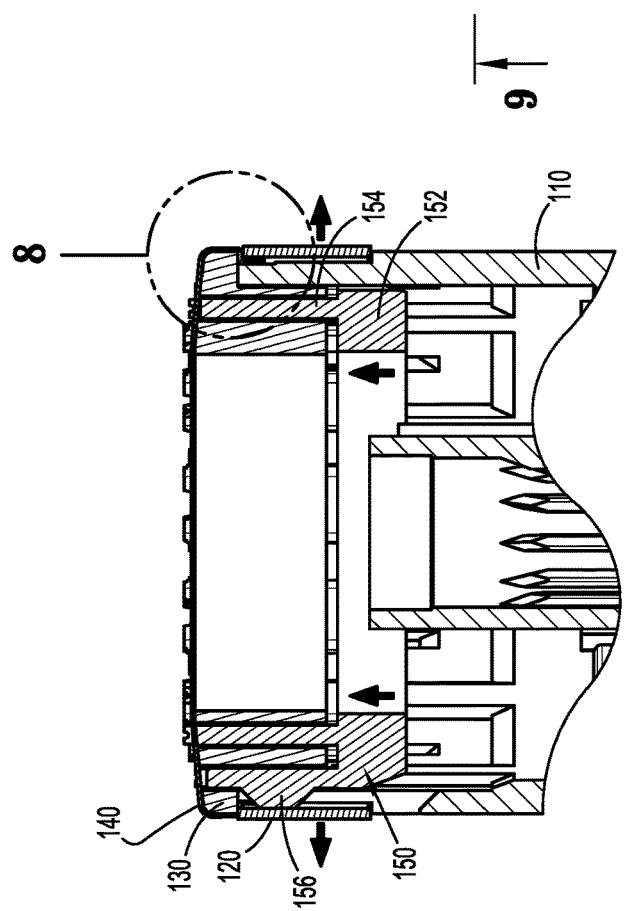
FIG. 8
FIG. 7

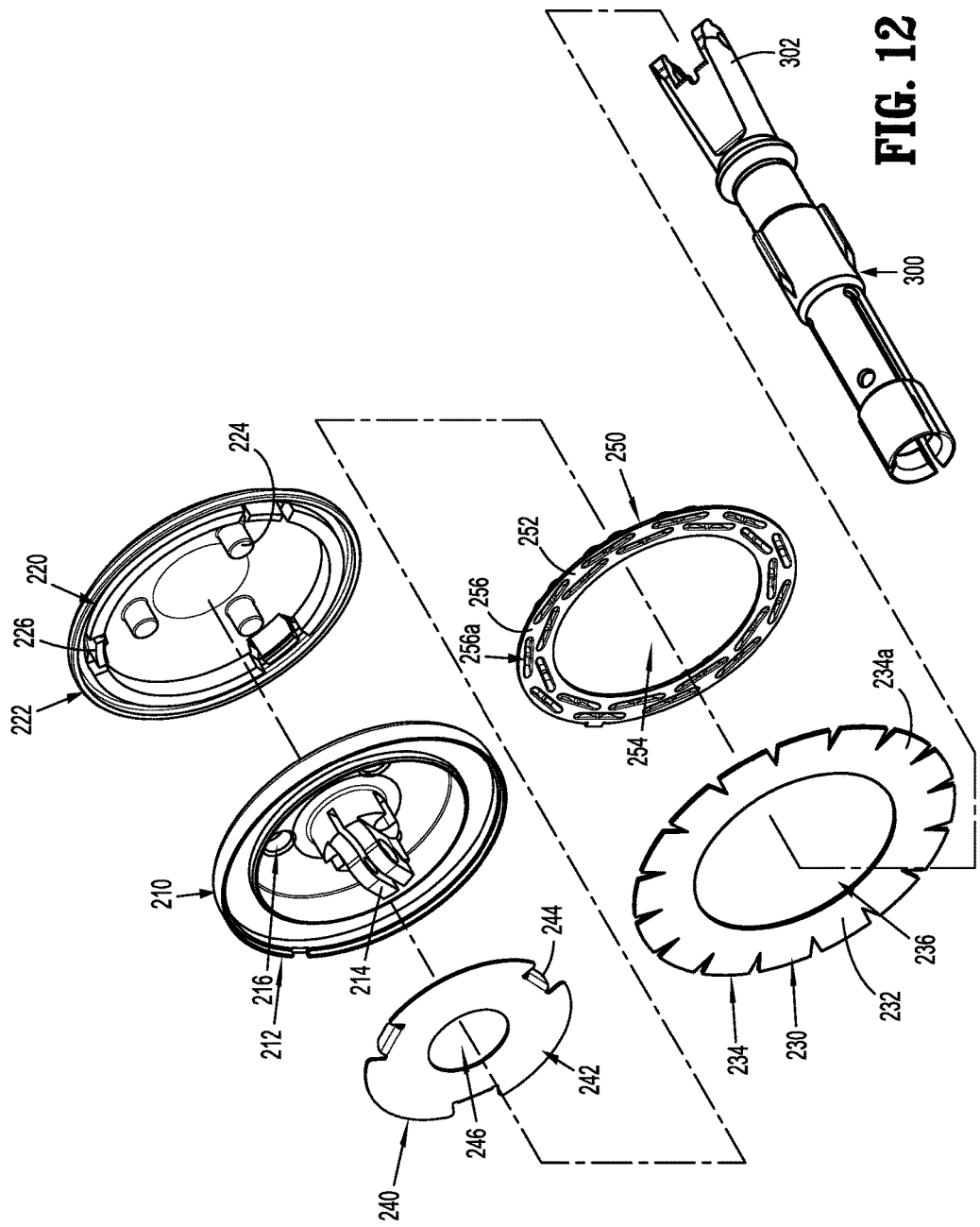

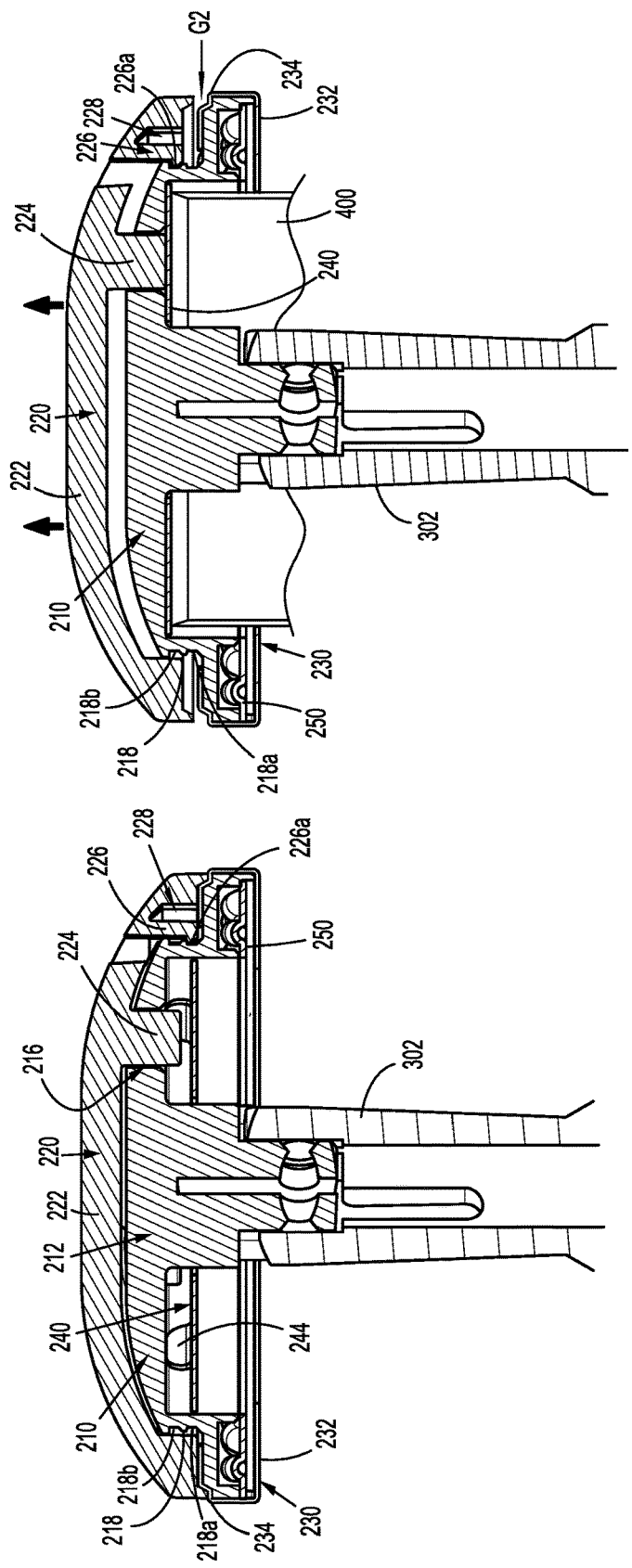

BUTTRESS ATTACHMENT FOR CIRCULAR STAPLING DEVICE

CROSS REFERENCE TO RELATED APPLICATIONS

This application is a Divisional of U.S. patent application Ser. No. 13/758,120, filed Feb. 4, 2013, now U.S. Pat. No. 9,414,839, the entire content of which is incorporated by reference herein.

TECHNICAL FIELD

The present disclosure relates to surgical stapling devices and, more particularly, to structures and methods for removably attaching buttress material to circular surgical stapling devices for use in anastomosis procedures.

BACKGROUND

Fasteners have traditionally been used to replace suturing when joining various body structures such as, for example, the bowel or bronchus. Surgical stapling devices employed to apply these fasteners are generally designed to simultaneously cut and seal tissue to reduce the time and risks involved with anastomosis procedures.

Circular surgical stapling devices are employed by surgeons to sequentially or simultaneously apply one or more surgical fasteners, e.g., staples or two-part fasteners, to body tissue for the purpose of joining segments of body tissue together and/or for the creation of anastomoses. Circular surgical stapling devices generally include an annular fastener cartridge assembly that supports a plurality of annular rows of fasteners, an annular anvil assembly operatively associated with the fastener cartridge assembly which provides a surface against which the fasteners are formed upon a firing of the circular stapling device, and an annular blade for cutting tissue.

For most procedures, the use of bare fasteners, with the fasteners in direct contact with the patient's tissue, is generally acceptable. The integrity of the tissue will normally serve to prevent the fasteners from tearing out of the tissue and compromising the sealing before healing has occurred. However, in some surgical operations buttress materials are employed by surgeons in combination with circular stapling devices to bridge, repair and/or reinforce tissue defects within a patient. In particular, buttress materials reduce the trauma suffered by the patient, reduce the instances of leakage, reduce the instances of bleeding, and create a relatively strong bond between adjacent body tissues.

Accordingly, there is a need for reliably and removably attaching buttress material onto a circular stapling device so that the buttress material does not interfere with the operation of the device, remains on the device until after the fasteners are fired, and is convenient and easy to install and use.

SUMMARY

According to one aspect, a circular stapling device includes a handle assembly, an elongate body that extends from the handle assembly, a cartridge assembly mounted on a distal end portion of the elongate body, and a circular cartridge buttress member.

The cartridge assembly includes a housing, a pusher member supported within the housing, a retaining ring member and a fastener cartridge body supported on the housing, and a circular cartridge buttress member. The fastener cartridge body has a tissue engaging surface that extends to an annular edge.

The pusher member is movable between a first position and a second position. The pusher member includes one or more ramp features extending radially outward from an outer surface of the pusher member. The one or more ramp features move the retaining ring member toward the radially expanded condition when the one or more ramp features engage an inner surface of the retaining ring member. The housing defines one or more channels that receive the one or more ramps. The one or more ramps are movable in the one or more channels.

The retaining ring member is configured and arranged to move between a radially constricted condition and a radially expanded condition in response to movement of the pusher member. The housing defines a cutout in an outer surface thereof within which the retaining ring member is seated when the retaining ring member is disposed in the radially constricted condition.

The circular cartridge buttress member has a body portion and an extension portion. The body portion is supported on the tissue engaging surface of the fastener cartridge. The extension portion extends from the body portion and over the annular edge of the tissue engaging surface. The retaining ring member secures the extension portion against one or both of the fastener cartridge body and the housing when in the radially constricted condition. The retaining ring member releases the extension portion when the retaining ring member moves to the radially expanded condition in response to a movement of the pusher member from the first position to the second position so that the body portion of the cartridge buttress separates from the tissue engaging surface of the fastener cartridge body.

In embodiments, the retaining ring member is a split ring. The split ring includes a pair of ends, each end being disposed in at least relatively close approximation with one another when the split ring is disposed in the radially constricted condition. The ends separate from one another when the split ring is disposed in the radially expanded condition.

The split ring includes a plurality of spaced apart tabs extending from a top edge of a body of the split ring. The plurality of spaced apart tabs engages a bottom surface of the fastener cartridge body. A clearance is defined between adjacent tabs of the plurality of spaced apart tabs, the bottom surface of the fastener cartridge body, and the top edge of the body of the split ring. The extension portion of the cartridge buttress member includes a plurality of sections. The clearance is adapted to receive one or more sections of the extension portion to secure the one or more sections of the extension portion between the fastener cartridge body and the split ring. Movement of the pusher member into engagement with the split ring expands the split ring radially outwardly and creates a radial clearance sufficient to release the one or more sections of the extension portion from between the fastener cartridge body and the split ring so that the cartridge buttress member separates from the fastener cartridge body upon the firing of fasteners from the fastener retaining slots defined within the fastener cartridge body.

In accordance with another aspect, an anvil assembly includes a circular anvil head, an anvil cap, and a circular anvil buttress member. The circular anvil head has a first engaging feature and supports a crush ring member.

The anvil cap has a second engaging feature that connects with the first engaging feature of the anvil head to secure the anvil cap to the anvil head. The anvil cap is movable relative to the anvil head between an approximated position and an unapproximated position. The crush ring member is spaced from the second engaging feature when the anvil cap is disposed in the approximated position and movable into engagement with the second engaging feature to move the anvil cap to the unapproximated position.

The circular anvil buttress member includes a body portion and an extension portion that extends from the body portion. The body portion is supported on a tissue engaging surface of the anvil head. The extension portion is secureable between the anvil cap and the anvil head when the anvil cap is disposed in the approximated position. The extension portion is releasable from between the anvil cap and the anvil head when the anvil cap is disposed in the unapproximated position so that the body portion separates from the tissue engaging surface of the anvil head. In the unapproximated position, the anvil cap and the anvil head define a gap therebetween dimensioned to permit the extension portion to release from between the anvil cap and the anvil head. In the approximated position, the gap is dimensioned to enable the anvil cap and the anvil head to trap the extension portion therebetween.

The anvil cap includes a snap feature and the anvil head defines a first recess and a second recess. The snap feature is selectively positionable within one of the first recess and the second recess. The snap feature is positionable within the first recess when the anvil cap is disposed in the approximated position and is positionable within the second recess when the anvil cap is disposed in the unapproximated position. The first recess and the second recess are separated by a ramped partition. The snap feature cams over the ramped feature as the anvil cap moves from the approximated position to the unapproximated position. The snap feature flexes outwardly from the first recess as the snap feature cams over the ramped partition and flexes inwardly into the second recess after camming over the ramped partition. The snap feature maintains the anvil cap secured to the anvil head when the snap feature is disposed in the second recess. The snap feature defines an opening disposed radially outwardly of the snap feature that permits the snap feature to flex outwardly relative to a body of the anvil cap. In embodiments, the anvil cap includes a plurality of spaced apart snap features.

According to another aspect, a method for releasing an anvil buttress member from an anvil assembly of a circular stapling device includes the step of providing a circular stapling device including an elongate member having an end effector mounted on a distal end portion of the elongate body. The end effector includes an anvil assembly that includes an anvil head and an anvil cap that support an extension portion of an anvil buttress member therebetween so that a body portion of the anvil buttress member is supported on a tissue engaging surface of the anvil head. The method involves moving the anvil cap relative to anvil head to release the anvil buttress member from the anvil assembly.

The method includes releasing the extension portion of the anvil buttress member from being trapped between the anvil cap and the anvil head. One step involves moving a crush ring member supported on the anvil head into engagement with the anvil cap to move the anvil cap relative to the anvil head. Another step includes spacing the anvil cap and the anvil head relative to one another in response to engagement of the crush ring member with the anvil head to provide a gap between the anvil cap and the anvil head sufficient to enable the extension portion of the anvil buttress member to be released from between the anvil cap and the anvil head.

Other aspects, features, and advantages will be apparent from the description, drawings, and claims.

BRIEF DESCRIPTION OF DRAWINGS

The accompanying drawings, which are incorporated in and constitute a part of this specification, illustrate embodiments of the disclosure and, together with a general description of the disclosure given above and the detailed description given below, serve to explain the principles of the disclosure, wherein:

FIG. 4 is a partial side cross-sectional view of the cartridge assembly, the cartridge assembly being shown in a first configuration;

FIG. 5 is an enlarged cross-sectional view illustrating the indicated area of detail shown in FIG. 4;

FIG. 7 is a partial side cross-sectional view of the cartridge assembly, the cartridge assembly being shown in a second configuration;

FIG. 8 is an enlarged cross-sectional view illustrating the indicated area of detail shown in FIG. 7;

FIG. 12 is a perspective view, with parts separated, of the anvil assembly and the shaft member;

FIG. 13 is a cross-sectional view of the anvil assembly and a distal portion of the shaft member, the anvil assembly being shown in a first configuration;

FIG. 14 is a cross-sectional view of the anvil assembly and a distal portion of the shaft member, the anvil assembly being shown in a second configuration.

DETAILED DESCRIPTION

Figure 2:
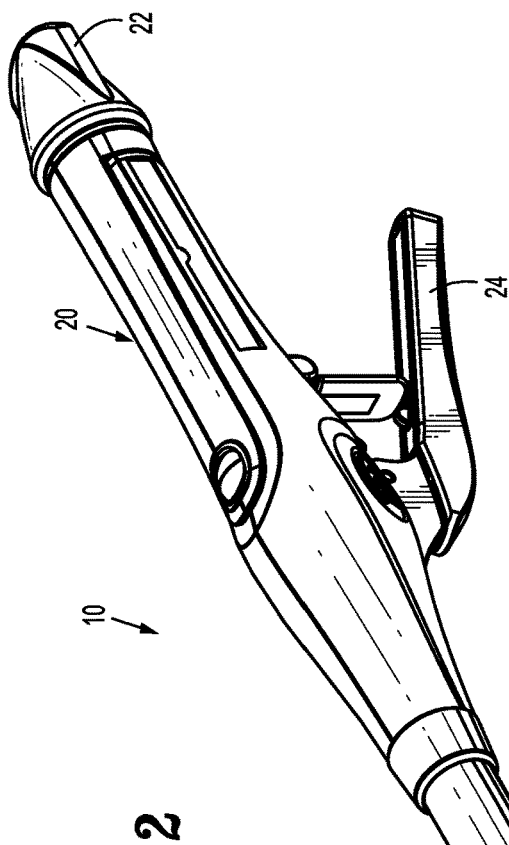
FIG. 2 is an enlarged perspective view illustrating the indicated area of detail shown in FIG. 1.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the clinician and the term "distal" refers to the end of the device that is farther from the clinician. In the following description, well-known functions or constructions are not described in detail to avoid obscuring the present disclosure in unnecessary detail.

Figure 1:
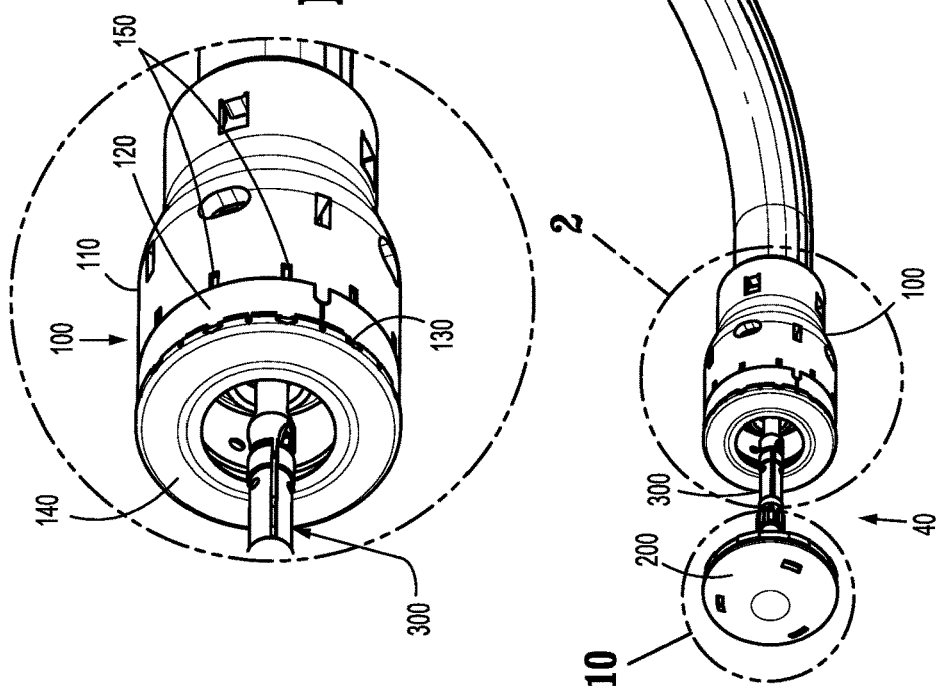
FIG. 1 is a perspective view of a circular surgical stapling device according to the present disclosure.

Referring initially to FIG. 1, a circular surgical stapling device for use with a buttress material is disclosed herein and is generally designated as 10. In embodiments, the surgical stapling device 10 is adapted for reuse and in certain embodiments; the surgical stapling device 10 is adapted for a single use and can be disposable.

The circular stapling device 10 includes a handle assembly 20, a tubular elongate body 30, and an end effector 40. The handle assembly 20 includes a rotatable advancing member 22 and a pivotable trigger member 24 that are operatively coupled to any number of drivers supported by the surgical stapling device 10 to effectuate a firing of the surgical stapling device 10.

In any of the embodiments disclosed herein, the handle assembly may include a source of power, such as a motor and battery, may be connectable to an external power source, or a remote control unit.

The elongate body 30 extends distally from a distal end portion of the handle assembly 20 to a proximal end portion of the end effector 40 so that the elongate body 30 is disposed between the handle assembly 20 and the end effector 40. In some embodiments, the elongate body 30 has a linear shape along the length of the elongate body 30, and in certain embodiments, the elongate body 30 has a curved shape along the length of the elongate body 30.

The end effector 40 includes a fastener cartridge assembly 100, an anvil assembly 200, and a shaft 300. The shaft 300 includes a proximal end portion that is secured to the fastener cartridge assembly 100 and a distal end portion that is secured to the anvil assembly 200. In certain embodiments, the fastener cartridge assembly 100 and/or the anvil assembly 200 may be replaced and the circular stapling device 10 may be reused. The end effector 40 supports a knife assembly with a substantially cylindrical knife 400 (FIG. 14) adapted to cut tissue.

Reference may be made to U.S. Pat. No. 5,915,616 to Viola et al. and commonly owned U.S. Patent Application Publication No. 2011/0174099, the entire contents of which are incorporated herein by reference, for a detailed discussion of the construction and operation of exemplary circular stapling devices.

Figure 3:
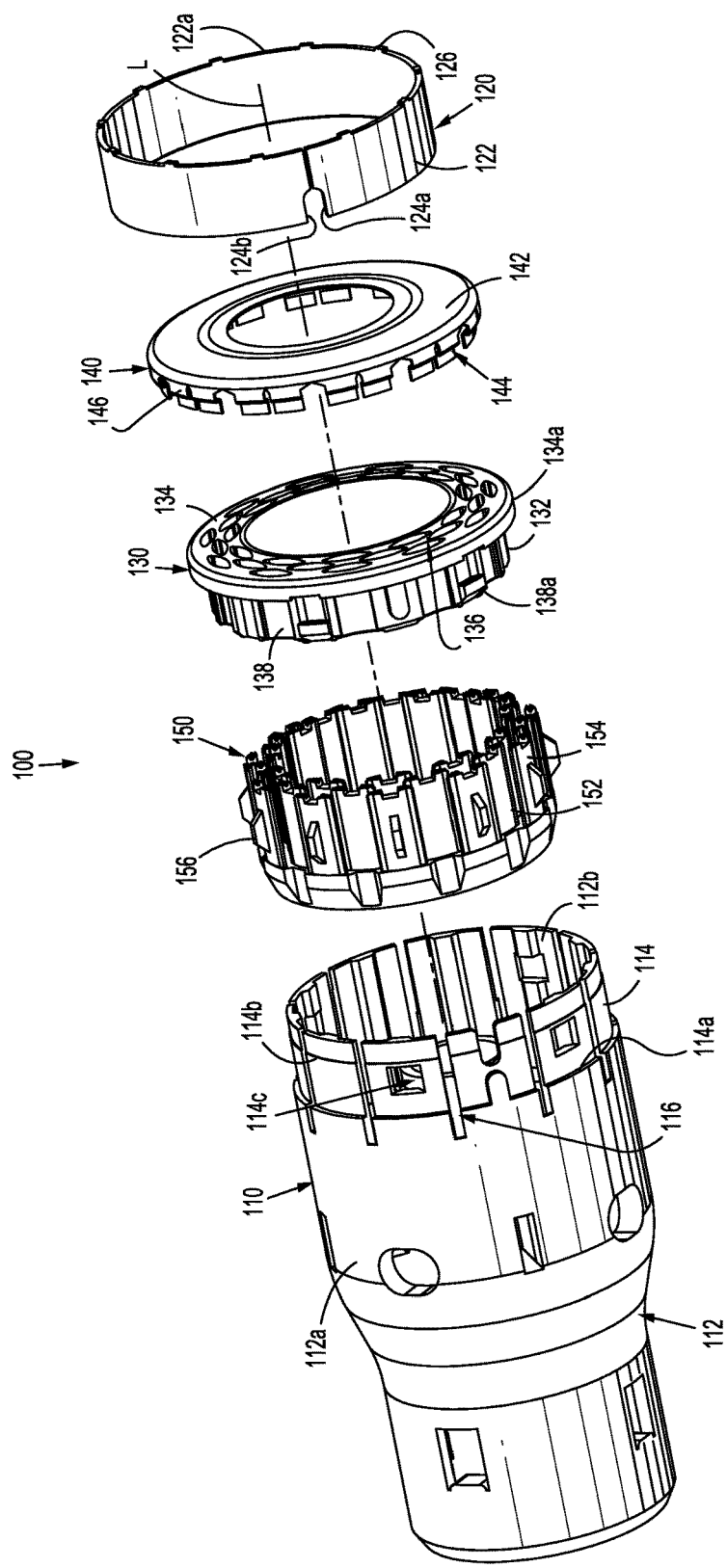
FIG. 3 is an enlarged perspective view, with parts separated, of a cartridge assembly of the presently disclosed circular surgical stapling device.
Figure 6:
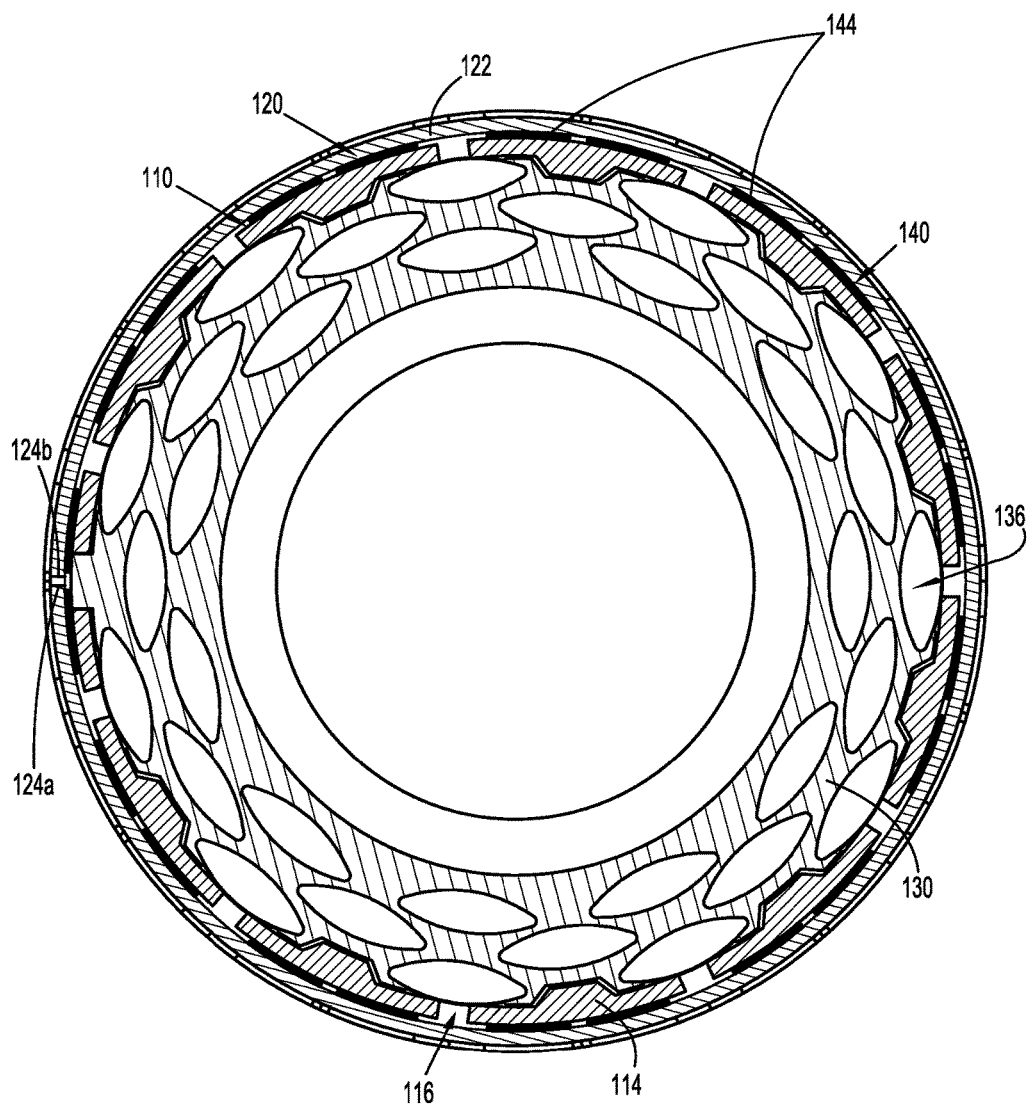
FIG. 6 is a top cross-sectional view of the cartridge assembly taken along line 6-6 of FIG. 5.
Figure 9:
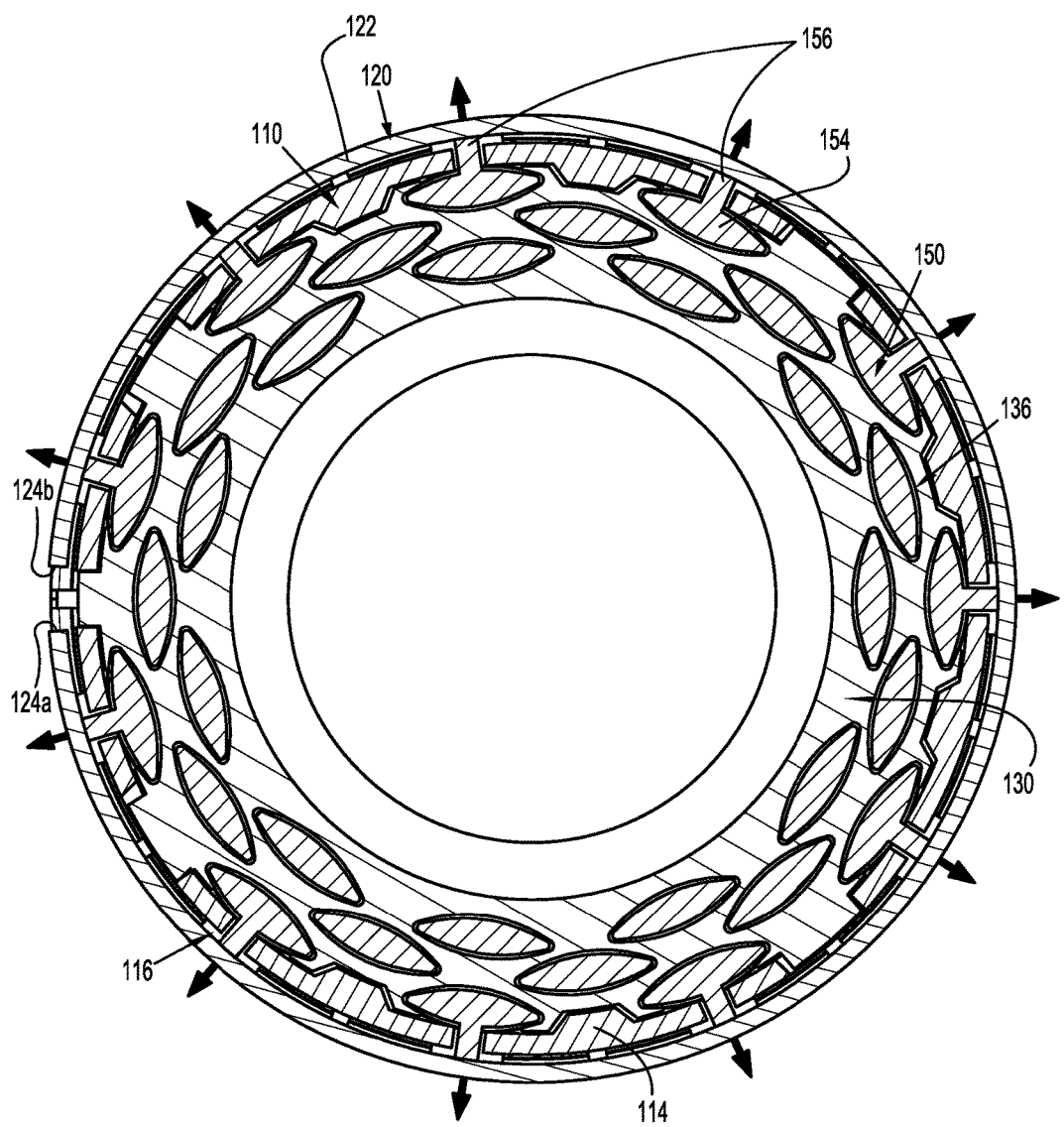
FIG. 9 is a top cross-sectional view of the cartridge assembly taken along line 9-9 of FIG. 8.
Figure 10:
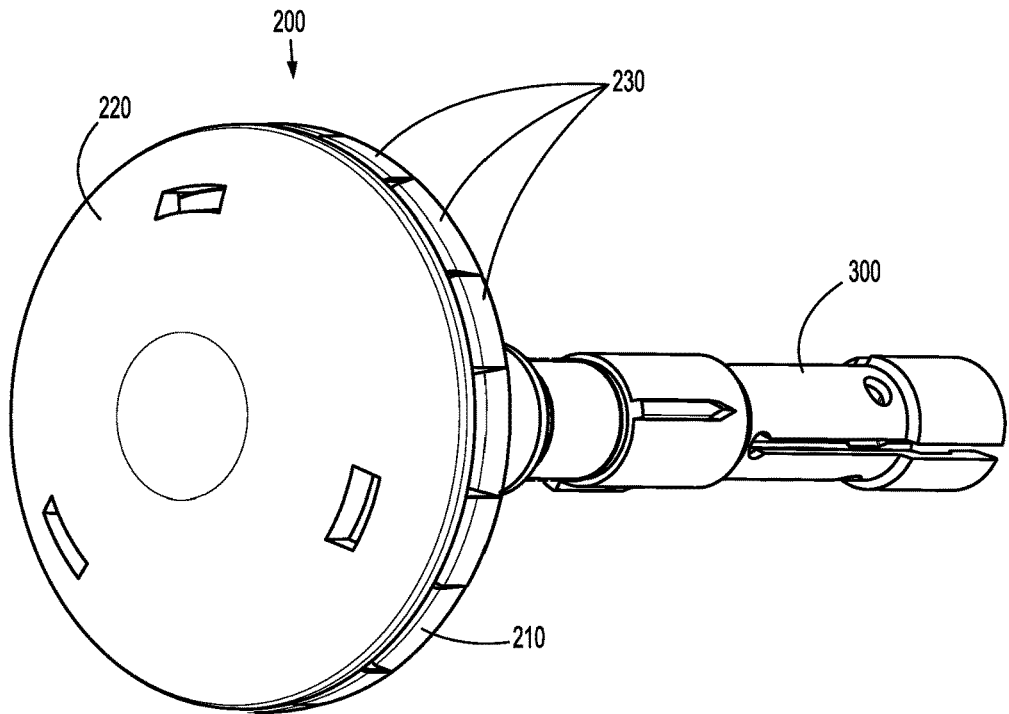
FIG. 10 is a top perspective view of an anvil assembly and a shaft member of the presently disclosed circular surgical stapling device.
Figure 11:
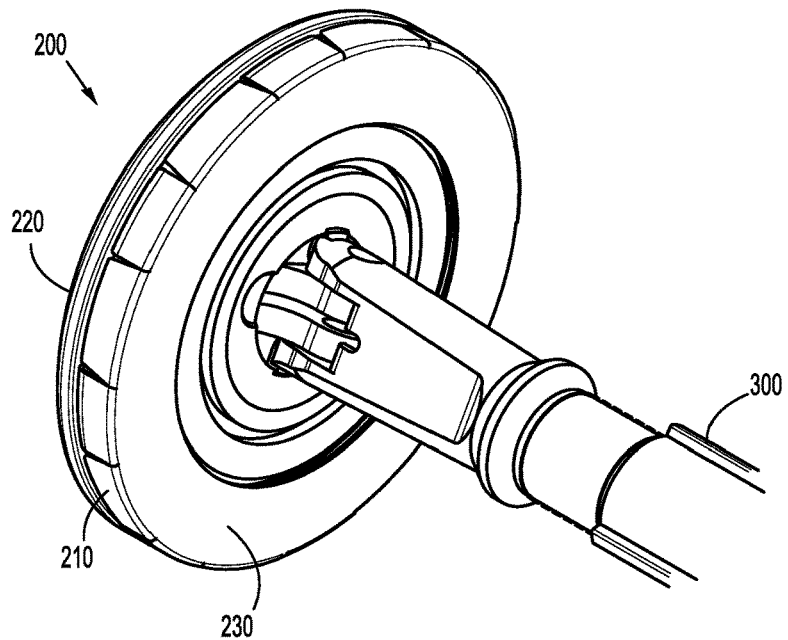
FIG. 11 is a bottom perspective view of the anvil assembly and a portion of the shaft member.

Turning now to FIGS. 2-3, the cartridge assembly 100 includes a housing 110, a retaining ring member 120, a fastener cartridge body 130, a circular cartridge buttress 140, and a pusher member 150.

The housing 110 has a generally tubular shell body 112 with an outer surface 112a and an inner surface 112b. The shell body 112 extends distally to a plurality of arms 114 that extend radially about the circumference of the distal end portion of the shell body 112. Each arm 114 includes a first shoulder 114a and a second shoulder 114b that are recessed from the outer surface of the housing 110. Each shoulder may be recessed to any suitable depth. For example, the first shoulders 114a and the second shoulders 114b may be recessed at different depths from the outer surface of the housing 110. In particular, the first shoulders 114a may be recessed at a first depth to define a first annular cutout, channel, or race and the second shoulders 114b may be recessed at a second depth to define a second annular cutout, channel, or race different from the first annular cutout. The first annular cutout is dimensioned to receive the retaining ring member 120 and the second annular cutout is dimensioned to receive at least part of an extension portion 144 of the cartridge buttress member 140 as described in greater detail below. Each arm 114 is disposed in spaced-apart relationship with adjacent arms 114. Adjacent arms 114 define a channel 116 therebetween. At least some of the arms 114 define an opening 114c that extends through the respective arm 114.

The retaining ring member 120 is supported on the outer surface 112a of the housing 110 and is dimensioned to move relative to the tubular shell body 112 of the housing 110 between a radially constricted condition and a radially expanded condition in response to movement of the pusher member 150 to selectively retain or release the circular cartridge buttress 140 on or from the fastener cartridge body 130 as described in greater detail below. The retaining ring member 120 (e.g., a split ring) has an annular body 122 that extends radially between a pair of end portions 124 including a first end portion 124a and a second end portion 124b. In the radially constricted condition, the end portions 124 are in contact or are disposed in relatively close approximation with one another. As the retaining ring member 120 moves from the radially constricted condition to the radially expanded condition, the end portions 124 separate from one another such that the end portions 124 are spaced from one another in the radially expanded condition. Notably, any space between the end portions 124 that may be provided when the retaining ring member 120 is in the radially constricted condition is increased as the end portions 124 move toward the radially expanded condition.

As seen in FIG. 3, the retaining ring member 120 includes a plurality of spaced apart tabs 126 that extend from a top edge 122a of the body 122. The plurality of spaced apart tabs 126 are dimensioned to engage a bottom surface of the fastener cartridge body 130 such that a clearance is defined between adjacent tabs of the plurality of spaced apart tabs 126, the bottom surface of the fastener cartridge body 130, and the top edge 122a of the body 122 of the retaining ring member 120 when the plurality of spaced apart tabs 126 are engaged with the bottom surface of the fastener cartridge body 130. The clearance is dimensioned to receive a part or parts of an extension portion 144 of the circular cartridge buttress member 140 to secure the extension portion 144 between the fastener cartridge body 130 and the ring retaining member 120.

The fastener cartridge body 130 is supported on the housing 110 and includes an annular body 132. The annular body 132 is received in a distal end portion of the housing 110. Fastener cartridge body 130 includes a tissue engaging surface 134 that extends to an annular edge 134a. A plurality of fastener retaining slots 136 are defined within the tissue engaging surface 134 and arranged in one or more concentric and/or annular arrays. Each fastener retaining slot 136 is dimensioned to receive a fastener 50 (FIG. 4). The annular body 132 includes one or more detents 138a that extends from a sidewall 138 thereof. Each detent 138a is dimensioned to engage an opening 114c of the arms 114 of the housing 110 to secure the fastener cartridge body 130 to the distal end portion of the housing 110.

As seen in FIGS. 4 and 5, the circular cartridge buttress 140 is selectively supported on the fastener cartridge body 130 and includes a body portion 142 and an extension portion 144 that extends radially outwardly from the body portion 144. The extension portion 144 may include any number of sections. The body portion 142 is dimensioned to overlie the tissue engaging surface 134 of the fastener cartridge body 130. The extension portion 144 includes a plurality of spaced apart fingers 146 arranged annularly about the body portion 144. The extension portion 144 is dimensioned to extend over the annular edge 134a of the tissue engaging surface 134 of the fastener cartridge body 130 and is positionable adjacent to the shoulder 114b of the housing 110 between the outer surface of one or more of the arms 114 of the housing 110 and the inner surface of the retaining ring member 120 for securement between the retaining ring member 120 and the housing 110. The extension portion 144 may be dimensioned to contact the shoulder 114b. As appreciated, the retaining ring member 120 secures the extension portion 144 against one or both of the fastener cartridge body 130 and the housing 110 when the retaining ring member 120 is in the constricted condition and releases the extension portion 144 when the retaining ring member 120 moves to the expanded condition. For example, the retaining ring member and pusher member can be arranged so that the retaining ring member moves to the expanded condition in response to a movement of the pusher member 150 from a proximal position to a distal position as described in greater detail below.

The pusher member 150 is movably mounted within housing 110 between proximal and distal positions. The pusher member 150 includes an annular pusher body 152 that has a plurality of pushers 154 disposed in a concentric and/or annular array about the pusher body 152. One or more ramps 156 extend radially outwardly from an outer surface of at least some of the pushers 154.

Turning now to FIGS. 10-14, the anvil assembly 200 includes a circular anvil head 210, an anvil cap 220, a circular anvil buttress member 230, a crush ring member 240, and an anvil plate 250.

The circular anvil head 210 includes a head body 212 that supports the crush ring member 240 and the anvil plate 250 on a proximal surface of the head body 212. The head body 212 has a connector 214 extending proximally from the head body 212. The connector 214 is dimensioned to operatively couple to a distal end portion 302 of the shaft member 300. One or more engaging passages 216 are defined by the head body 212 and extend through the head body 212. A distal surface of the head body 212 includes one or more ramped partitions 218 that separate a first recess 218a and a second recess 218b defined on opposite sides of ramped partition 218.

The anvil cap 220 includes a cap body 222 that is supported on the distal surface of the anvil head 210. The cap body 222 includes one or more engaging features 224 and one or more snap features 226 that extend proximally from the cap body 222. The snap feature 226 includes a tooth 226a that extends inwardly. The first and second recesses 218a, 218b of the anvil head 210 are each dimensioned to receive the tooth 226a to facilitate securement of the anvil cap 220 to the anvil head 210. The cap body 222 defines an opening 228 dimensioned to enable the snap feature 226 to flex radially outwardly to permit the anvil cap 220 to move relative to the anvil head 210 between approximated and unapproximated positions. (See FIG. 14, for example).

The anvil plate 250 secures to the proximal surface of the anvil head 210 and has an annular body 252 that defines an opening 254 therethrough. The annular body 252 has a tissue engaging surface 256 that defines a plurality of fastener forming pockets 256a. The plurality of fastener forming pockets 256a is arranged in an annular array about the tissue engaging surface 256 of the annular body 252.

The circular anvil buttress member 230 is selectively supported on the anvil plate 250 and has an annular body portion 232 and an extension portion 234 that extends radially from the body portion 232. The body portion 232 is dimensioned to overlie the tissue engaging surface 256 of the anvil plate 250 and defines a central opening 236 therethrough. The extension portion 234 includes a plurality of spaced apart tabs 234a that extend radially outwardly about the body portion 232. The plurality of spaced apart tabs 234a are selectively positionable between the proximal surface of the anvil cap 220 and the distal surface of the anvil head 210 to selectively secure the annular body portion 232 against the tissue engaging surface 256 of the anvil plate 250 when the anvil cap 220 is disposed in the approximated position. As described in greater detail below, the extension portion 234 is releasable from the between the anvil cap 220 and the anvil head 210 when the anvil cap 220 is moved to the unapproximated position so that the body portion 232 separates from the tissue engaging surface 256 of the anvil plate 250.

The crush ring member 240 is supported on the anvil head 210 and includes a generally annular body 242 having a plurality of tab members 244 that secure to a proximal surface of the anvil head 210 and extend from the body 242 at radially spaced locations along an outer surface of the body 242. The crush ring member 240 is dimensioned to be spaced from the one or more engaging features 224 of the cap body 222 when the anvil cap 220 is disposed in the approximated position and movable into engagement with the one or more engaging features 224 when the anvil cap 220 is moved to the unapproximated position. The annular body 242 defines an aperture 246 therethrough that is dimensioned to receive the connector 214 of the head body 212 when the crush ring member 240 is secured to the anvil head 210.

During operation of the surgical stapling device 10, the anvil assembly 200 and the cartridge assembly 100 are approximated by the actuation of advancing member 22 until the anvil assembly 200 and the cartridge assembly 100 are suitably clamped against tissue of a patient. The trigger member 24 is then actuated to fire the surgical stapling device 10.

With reference to FIGS. 4-9, the pusher member 150, upon a firing of the surgical stapling device 10, is distally advanced from a proximal position by a drive assembly (not shown). As the pusher member 150 distally advances, the plurality of pushers 150 advance through the fastener retaining slots 136 to engage and dispense the fasteners 50 supported within the fastener retaining slots 136.

Additionally, as the pusher member 150 distally advances, the ramps 156 thereof slide through the channels 116 of the housing 110 and into engagement with the inner surface of the retaining ring member 120. The ramps 156 push the retaining ring member 120 radially outwardly from the radially constricted condition to the radially expanded condition of the retaining ring member 120. As the retaining ring member 120 moves to the radially expanded condition, a radial clearance or gap "G1" is created between the retaining ring member 120 and the outer surface of the housing 110 which frees the extension portion 144 of the cartridge buttress 140. The distal driving force provided to the fasteners 50 from the pusher member 150 is imparted to the body portion 142 of the circular cartridge buttress 140 which releases the circular cartridge buttress 140 by drawing the extension portion 144 of the circular cartridge buttress 140 distally through the created space or gap "G1." Upon release of the extension portion 144 of the cartridge buttress 140, the body portion 142 is separable from the tissue engaging surface 134 of the fastener cartridge body 130.

Figure 15:
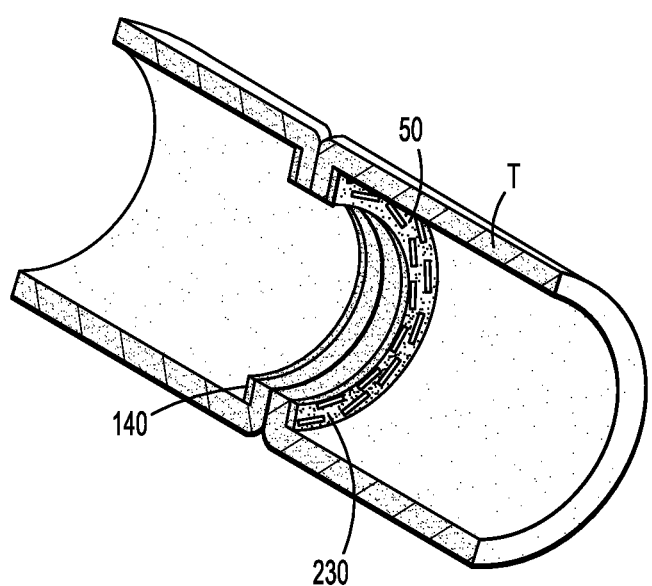
FIG. 15 is a cross-sectional perspective view of an anastomotic tissue site, the anastomotic tissue site being shown with buttress material of the presently disclosed circular stapling device secured thereto during a surgical procedure effectuated with the presently disclosed circular stapling device.

Referring also to FIGS. 13-15, the driving force imparted on the fasteners 50 drives the legs of the fasteners 50 through cartridge buttress member 140, the clamped tissue "T", and anvil buttress member 230 until the legs of the fasteners 50 are formed within the fastener forming pockets 256a of the anvil plate 250 to secure the cartridge buttress 140 and the anvil buttress member 230 to the tissue "T" with the fasteners 50. The knife 400 is simultaneously thereafter advanced into the anvil assembly 200 to sever the tissue "T" and to distally advance the crush ring member 240. The distal movement of the crush ring member 240 drives the crush ring member 240 into engagement with the one or more engaging features 224 of the anvil cap 220 and separates the proximal surface of the cap body 222 of the anvil cap 220 from the distal surface of the head body 212 of the anvil head 210. In particular, the teeth 226a of the snap features 226 cam against the ramped partitions 218 so that each snap feature 226 flexes radially outwardly into the opening 228 of the cap body 222 from the first recess 218a of the head body 212 to enable the anvil cap 220 to separate from the anvil head 210 as the anvil cap 220 moves from the approximated position to the unapproximated position. After camming over the ramped partitions 218, the teeth 226a of the snap features 226 snap or flexes radially inwardly into the second recess 218b of the head body 212 to maintain the anvil cap 220 secured to the anvil head 210. The separation of the cap body 222 and the head body 212 creates a space or gap "G2" between the proximal surface of the cap body 222 and a distal surface of the head body 212 to free the extension portion 234 of the anvil buttress member 230 from between the anvil head 210 and the anvil cap 220 so that both of the anvil buttress member 230 and the cartridge buttress member 140 are secured to the tissue "T" independent of the surgical stapling device 10.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, in any of the embodiments disclosed herein, one or more curved arrays of staples can be provided in the fastener cartridge. Circular fastener cartridges, and curved fastener cartridges are contemplated as are two or three rows of staples. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

The invention claimed is:

1. An anvil assembly, comprising:
a circular anvil head having a first engaging feature and supporting a crush ring member;
an anvil cap having a second engaging feature that connects with the first engaging feature of the anvil head to secure the anvil cap to the anvil head, the anvil cap being movable relative to the anvil head between an approximated position and an unapproximated position, the crush ring member being spaced from the second engaging feature when the anvil cap is disposed in the approximated position and movable into engagement with the second engaging feature to move the anvil cap to the unapproximated position; and
a circular anvil buttress member including a body portion and an extension portion that extends from the body portion, the body portion supported on a tissue engaging surface of the anvil head, the extension portion being secureable between the anvil cap and the anvil head when the anvil cap is disposed in the approximated position, the extension portion being releasable from between the anvil cap and the anvil head when the anvil cap is disposed in the unapproximated position so that the body portion separates from the tissue engaging surface of the anvil head.

2. The anvil assembly of claim 1, wherein the anvil cap includes a snap feature and the anvil head defines a first recess and a second recess, the snap feature being selectively positionable within one of the first recess and the second recess, the snap feature being positionable within the first recess when the anvil cap is disposed in the approximated position and being positionable within the second recess when the anvil cap is disposed in the unapproximated position.

3. The anvil assembly of claim 2, wherein the first recess and the second recess are separated by a ramped partition, the snap feature camming over the ramped partition as the anvil cap moves from the approximated position to the unapproximated position.

4. The anvil assembly of claim 3, wherein the snap feature flexes outwardly from the first recess as the snap feature cams over the ramped partition and flexes inwardly into the second recess after camming over the ramped partition, the snap feature maintaining the anvil cap secured to the anvil head when the snap feature is disposed in the second recess.

5. The anvil assembly of claim 1, wherein the anvil cap includes a plurality of spaced apart snap features.

6. The anvil assembly of claim 1, wherein the anvil cap includes a snap feature, the anvil cap including a cap body that defines an opening disposed radially outwardly of the snap feature, the opening configured to enable the snap feature to flex outwardly relative to the cap body of the anvil cap.

7. The anvil assembly of claim 1, wherein in the unapproximated position, the anvil cap and the anvil head define a gap therebetween dimensioned to permit the extension portion to release from between the anvil cap and the anvil head.

8. The anvil assembly of claim 7, wherein in the approximated position, the gap is dimensioned to enable the anvil cap and the anvil head to trap the extension portion therebetween.

* * * * *